United States Patent
Hu et al.

(10) Patent No.: US 7,037,469 B2
(45) Date of Patent: May 2, 2006

(54) METHOD AND COMPOSITION FOR REDUCING CONTACT LENS SWELLING

(75) Inventors: Zhenze Hu, Pittsford, NY (US); Joseph C. Salamone, Fairport, NY (US); Dharmendra Jani, Fairport, NY (US)

(73) Assignee: Bausch & Lomb, Inc., Rochester, NY (US)

( * ) Notice: Subject to any disclaimer, the term of this patent is extended or adjusted under 35 U.S.C. 154(b) by 0 days.

(21) Appl. No.: 10/392,743

(22) Filed: Mar. 19, 2003

(65) Prior Publication Data

US 2004/0186028 A1    Sep. 23, 2004

(51) Int. Cl.
*A61L 2/18*   (2006.01)
*C11D 1/72*   (2006.01)
*C11D 3/37*   (2006.01)

(52) U.S. Cl. .................. 422/28; 510/112; 510/413; 510/421; 510/475; 134/42

(58) Field of Classification Search ................ 510/112, 510/413, 421, 475; 134/42; 422/28
See application file for complete search history.

(56) References Cited

U.S. PATENT DOCUMENTS

| | | | |
|---|---|---|---|
| 4,748,189 A | 5/1988 | Su et al. ..................... 514/781 |
| 4,786,436 A | 11/1988 | Ogunbiyi et al. ........... 252/352 |
| 5,209,865 A | 5/1993 | Winterton et al. ..... 252/174.22 |
| 5,401,327 A | 3/1995 | Ellis et al. ..................... 134/42 |
| 5,604,189 A * | 2/1997 | Zhang et al. ................ 510/112 |
| 5,773,396 A * | 6/1998 | Zhang et al. ................ 510/115 |
| 6,153,568 A * | 11/2000 | McCanna et al. ........... 510/112 |
| 6,274,133 B1* | 8/2001 | Hu et al. .................. 424/78.04 |
| 6,323,165 B1* | 11/2001 | Heiler et al. ................. 510/112 |
| 6,369,112 B1* | 4/2002 | Xia ............................. 514/635 |
| 6,440,366 B1 | 8/2002 | Salpekar et al. .............. 422/40 |
| 6,702,983 B1* | 3/2004 | Hu et al. ....................... 422/1 |

FOREIGN PATENT DOCUMENTS

WO   WO 02/34308      5/2002
WO   WO 2004/030715   4/2004

* cited by examiner

*Primary Examiner*—Brian P. Mruk
(74) *Attorney, Agent, or Firm*—Paul Lavoie; Craig Larson; Denis Polyn (57) ABSTRACT

The present invention is directed to an ophthalmic solution for soft contact lenses for controlled release of polyethers into an eye's tear film. Polyether components of the subject solution are released from the soft contact lens material matrix over long time periods to produce longer lasting wetting performance, improved lubricity, improved end-of-the-day comfort and reduced feeling of dryness from wearing contact lenses. The present invention also includes the use of cationic polyelectrolytes for controlling the swelling of hydrogel contact lenses typically caused by the absorption of high concentrations of polyethers.

16 Claims, 4 Drawing Sheets

METHOD AND COMPOSITION FOR REDUCING CONTACT LENS SWELLING

FIELD OF THE INVENTION

The present invention relates to a solution and a method of using the solution for absorption and controlled release of comforting components of the solution by hydrogel biomaterials to controll lens swelling and preserve visual acuity. More particularly, the present invention relates to an ophthalmic solution comprising polyethers that exhibit ready absorption into hydrogel biomaterials, such as that of a contact lens, and slow release over a period of time in an aqueous environment for longer lasting wetting performance. The ophthalmic solution of the present invention includes at least one cationic polyelectrolyte that functions to control lens swelling caused by the absorption of high concentrations of polyethers.

BACKGROUND OF THE INVENTION

Contact lenses in wide use today fall into two general categories. First, there are the hard or rigid type lenses that are formed from materials prepared by the polymerization of acrylic esters, such as poly(methyl methacrylate) (PMMA). Secondly, there are the gel, hydrogel or soft type lenses made by polymerizing such monomers as 2-hydroxyethyl methacrylate (HEMA) or, in the case of extended wear lenses, made by polymerizing silicon-containing monomers or macromonomers. Solutions that wet lenses before insertion into the eye are required for both the hard and soft types of contact lenses, although the formulations of the solutions for hard and soft type lenses have tended to differ based on the different desired properties of the solutions. Regardless of lens type, after contact lenses are inserted in the eye, ophthalmic solutions for rewetting, lubricating, and/or enhancing wearer comfort are sometimes applied to the eye by means of a drop dispenser.

Isotonic solutions for improving the comfort of wearing soft contact lenses by being added directly to the contact lens while in the eye are known. Such solutions typically contain viscosity enhancing agents, lubricants, surfactants, buffers, preservatives, and salts. For example, Sherman discloses in U.S. Pat. No. 4,529,535 a rewetting solution that is particularly useful for rigid silicone copolymer contact lenses, including extended wear lenses. In one embodiment, the rewetting solution contains the combination of hydroxyethylcellulose, poly(vinyl alcohol) and poly(N-vinylpyrrolidone).

Ogunbiyi et al. disclose in U.S. Pat. No. 4,786,436 a wetting solution comprising collagen and other demulcents such as hydroxyethylcellulose, methylcellulose, carboxymethylcellulose, hydroxypropylmethylcellulose, hydroxypropylcellulose and the like.

Su et al. disclose in U.S. Pat. No. 4,748,189 ophthalmic solutions for improving the exchange of fluid in the area underneath the hydrogel contact lens to allow tear exchange to occur, thereby preventing the accumulation of waste matter and debris under the lens. The solution contains a hydrogel flattening agent, for example, urea, glycerin, propylene glycol, sorbitol, or an amino-ethanol. Surfactants that are useful in the solution include poloxamer and tyloxapol. Suitable lubricants include hydroxyethylcellulose, poly(vinyl alcohol) and poly(N-vinylpyrrolidone).

Winterton et al. disclose in U.S. Pat. No. 5,209,865 a conditioning solution for contact lenses that comprises a combination of a poloxamine and a poloxamer surfactant, each having an HLB (hydrophilic-lipophilic balance) of seven or below. The solution according to the invention forms a uniform hydrophilic film on a lens surface for which proteins have very little affinity. As such, a contact lens contacted by the solution is said to have a coating that provides a prophylactic effect to the lens.

Zhang et al. disclose in U.S. Pat. No. 5,604,189 and U.S. Pat. No. 5,773,396 a composition for cleaning and wetting contact lenses comprising (i) a non-amine polyethyleneoxy-containing compound having an HLB of at least about 18, (ii) a surface active agent having cleaning activity for contact lens deposits that may have an HLB less than 18, and (iii) a wetting agent. Such compositions can include, as the wetting agent, an ethoxylated glucose derivative such as glucam as also disclosed in U.S. Pat. No. 5,401,327 to Ellis et al. Tyloxapol is a conventional surface active agent, used for example in Allergan's Complete™ multipurpose solution, which agent has cleaning activity for contact-lens deposits and has an HLB less than 18.

Unlike hard lenses, the soft type of contact lenses have a tendency to absorb significantly more fluids. While it is desirable to increase contact lens wearer comfort, it is not desirable to alter lens dimensions from the manufacturer's finished product specifications through lens swelling. Some compounds useful in ophthalmic solutions to increase contact lens wearer comfort can cause lens swelling resulting in decreased visual acuity.

It would, therefore, be desirable to have an ophthalmic solution that could be applied to a contact lens that not only rewets the lens but also provides controlled release wetting of the lens over a period of time until such lens is removed from the eye and cleaned or disposed. It would also be desirable to have an opthalmic solution that preserves visual acuity by controlling lens swelling typically associated with hydrogel contact lenses treated with high concentrations of polyethers.

SUMMARY OF THE INVENTION

The present invention relates to a solution and method for absorption and controlled release of comforting components of the solution by hydrogel biomaterials such as for example hydrogel biomaterials in the form of soft contact lenses, with controlled lens swelling to preserve visual acuity. The ophthalmic solution of the present invention comprises polyethers based upon poly(ethylene oxide)-poly(propylene oxide)-poly(ethylene oxide), i.e., (PEO-PPO-PEO), or poly (propylene oxide)-poly(ethylene oxide)-poly(propylene oxide), i.e., (PPO-PEO-PPO), or a combination thereof. PEO-PPO-PEO and PPO-PEO-PPO, such as for example poloxamers and poloxamines, are commercially available under the trade names Pluronics™, R-Pluronics™, Tetronics™ and R-Tetronics™ (BASF Wyandotte Corp., Wyandotte, Mich.). Polyethers in the subject ophthalmic solution exhibit ready absorption into hydrogel biomaterials such as those used in the manufacture of soft type contact lenses. Polyethers in the subject ophthalmic solution, after absorption into hydrogel biomaterials to a high concentration, exhibit slow release from the hydrogel biomaterials over a period of time in an aqueous environment. In accordance with the present invention, the one or more polyethers release slowly from a worn contact lens into an eye's tear film over a long time period to produce longer lasting wetting performance, improved lubricity, improved end-of-the-day comfort and reduced feeling of dryness from wearing contact lenses. The subject ophthalmic solutions, in addition to one or more polyethers, likewise include at least one cationic polyelectrolyte that functions to control lens swelling, particularly for anionic contact lenses. By controlling lens swelling, visual acuity is maintained. The subject ophthalmic solutions for multi-purpose treatment of contact lenses are effective in disinfecting contact lenses and rewetting contact lenses while in the eye, and are also suitable for use as lens packaging solutions.

Accordingly, it is an object of the present invention to provide an ophthalmic solution that provides longer lasting wetting performance for hydrogel contact lenses with controlled lens swelling.

Another object of the present invention is to provide a method for using an ophthalmic solution to provide longer lasting wetting performance for hydrogel contact lenses with controlled lens swelling.

Another object of the present invention is to provide an ophthalmic solution and a method for using the same that improves contact lens lubricity and end-of-the-day comfort.

Another object of the present invention is to provide an ophthalmic solution and method for using the same that reduces the feeling of eye dryness from wearing contact lenses.

Another object of the present invention is to provide an ophthalmic solution with comforting components that exhibit ready absorption into hydrogel biomaterials.

Still another object of the present invention is to provide an ophthalmic solution with comforting components that release slowly from hydrogel biomaterials into an aqueous environment.

These and other objectives and advantages of the present invention, some of which are specifically described and others that are not, will become apparent from the detailed description and claims that follow.

DETAILED DESCRIPTION OF THE INVENTION

Figure 1:
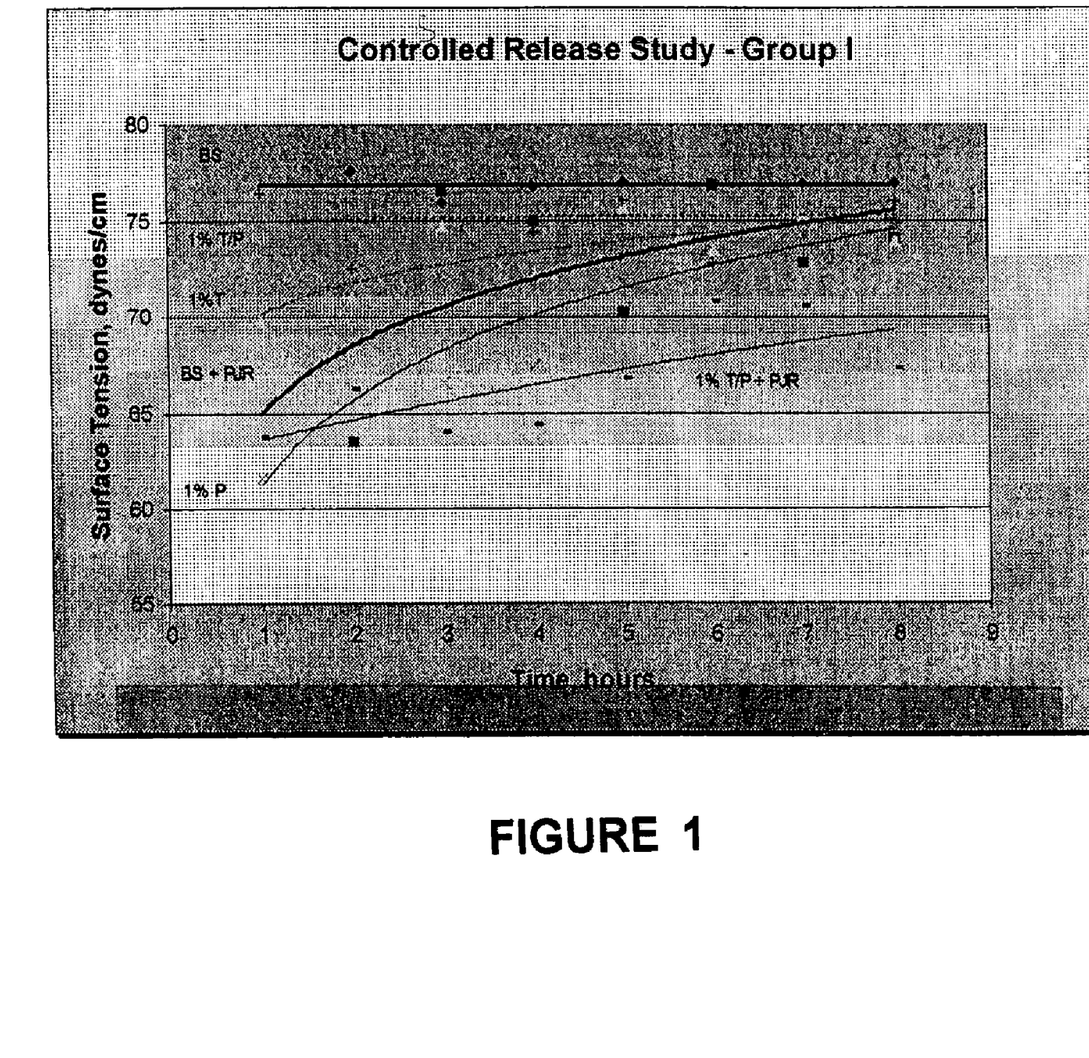
FIG. 1 is a graph of Group I controlled release of 1 percent polyether solutions.
Figure 2:
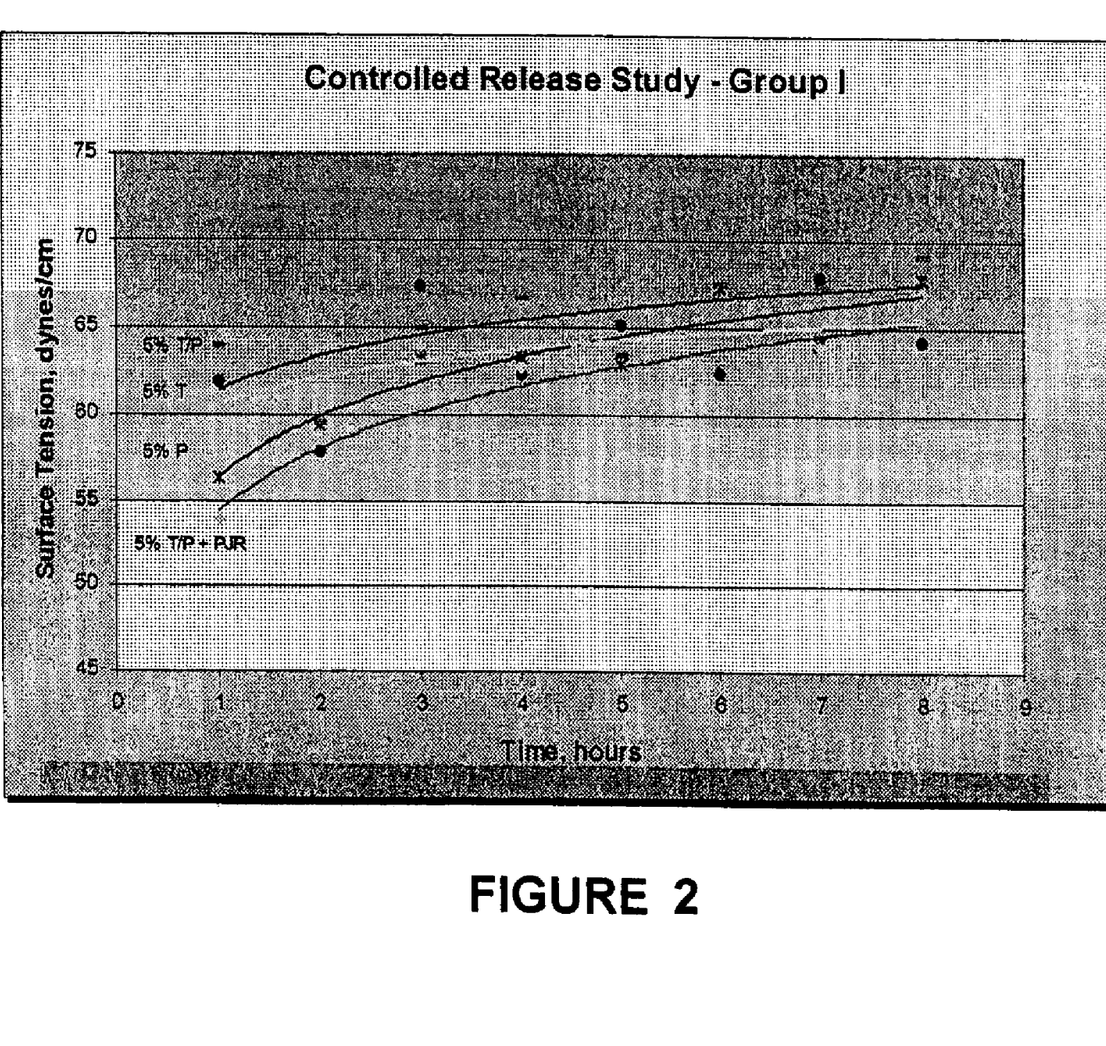
FIG. 2 is a graph of Group I controlled release of 5 percent polyether solutions.
Figure 3:
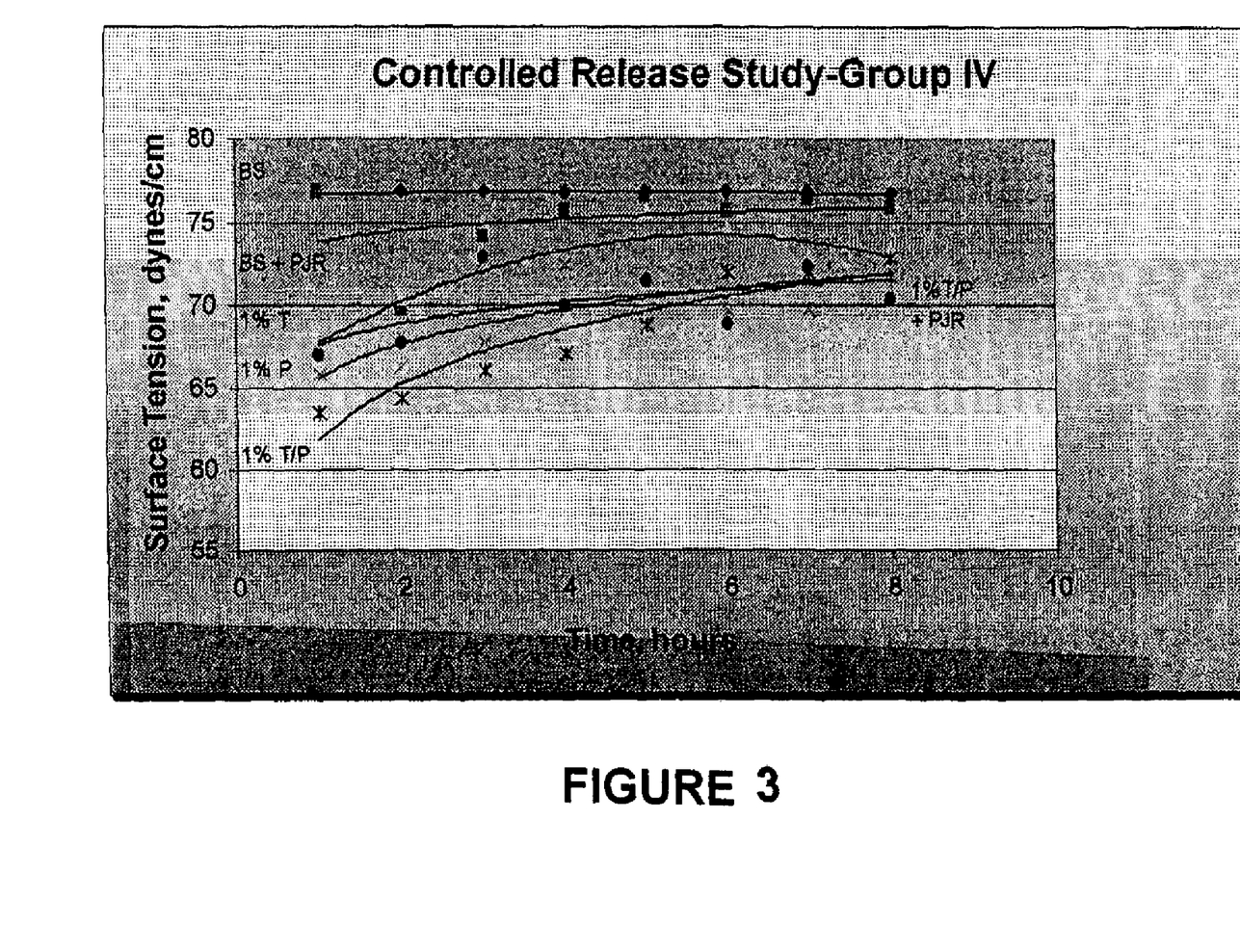
FIG. 3 is a graph of Group IV controlled release of 1 percent polyether solutions.
Figure 4:
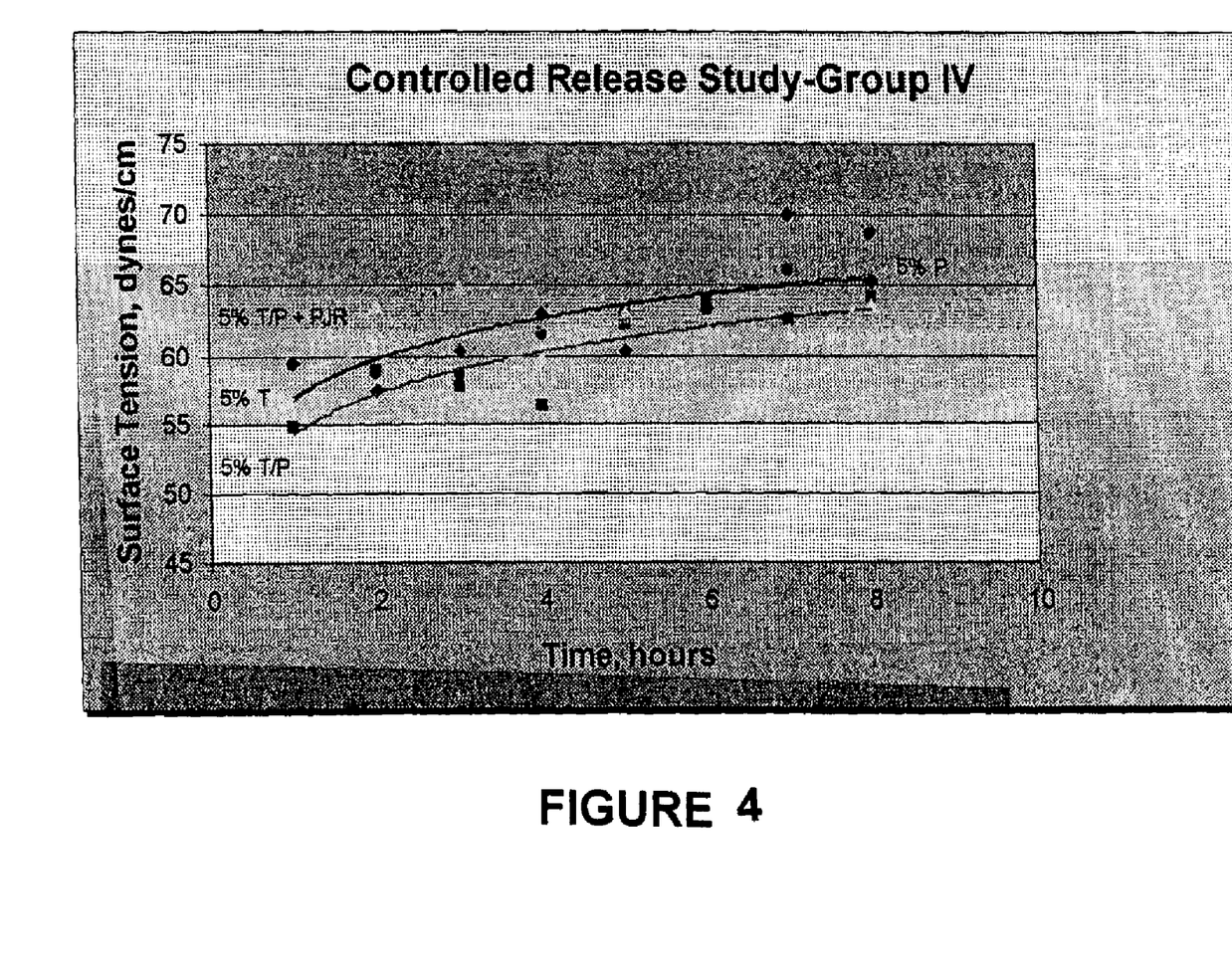
FIG. 4 is a graph of Group IV controlled release of 5 percent polyether solutions.

The present invention relates to a solution and a method of using the solution for absorption and controlled release of comforting components of the solution by hydrogel biomaterials such as for example hydrogel biomaterials in the form of soft contact lenses. Ophthalmic solutions of the present invention preferably comprise greater than approximately 1 percent by weight of polyethers based upon poly(ethylene oxide)-poly(propylene oxide)-poly(ethylene oxide), i.e., (PEO-PPO-PEO), or poly(propylene oxide)-poly(ethylene oxide)-poly(propylene oxide), i.e., (PPO-PEO-PPO), or a combination thereof. PEO-PPO-PEO and PPO-PEO-PPO are commercially available under the trade names Pluronics™, R-Pluronics™, Tetronics™ and R-Tetronics™ (BASF Wyandotte Corp., Wyandotte, Mich.). More preferably, the ophthalmic solution of the present invention comprises approximately 1.5 to 14 weight percent and most preferably between approximately 2 to 5 weight percent polyethers. Polyethers in the subject ophthalmic solution exhibit ready absorption into hydrogel biomaterials such as those used in the manufacture of soft type contact lenses. The subject absorption of polyethers into the material matrix of a contact lens described herein differs from the adsorption of surfactants onto the surface of a contact lens as disclosed by Salpekar et al., U.S. Pat. No. 6,440,366. Polyethers in the subject ophthalmic solution, after absorption to a high concentration by a hydrogel biomaterial, exhibit slow release from the hydrogel biomaterial over a period of time in an aqueous environment as illustrated in the graphs of FIGS. 1 through 4. In accordance with the present invention, the polyethers release slowly from a worn contact lens into an eye's tear film over a long time period to produce longer lasting wetting performance, improved lubricity, improved end-of-the-day comfort and reduced feeling of dryness from wearing contact lenses.

The subject ophthalmic solutions in addition to polyethers likewise include one or more, but at least one, cationic polyelectrolyte that functions to control lens swelling caused by the absorption of high concentrations of polyethers. By controlling lens swelling, visual acuity is maintained. Suitable cationic polyelectrolytes include for example but are not limited to polyquaternium 10, polyquaternium 11, polyquaternium 16, polyquaternium 44 and polyquaternium 46, but preferably polyquaternium 16 available under the trade name Luviquat™ FC 370 (BASF Wyandotte Corp.) or polyquaternium 10 available under the trade name Polymer JR (BASF Wyandotte Corp.). Preferably, the ophthalmic solution of the present invention comprises approximately 0.001 to 5 percent by weight and more preferably between approximately 0.01 to 0.5 percent by weight of one or more cationic polyelectrolytes for control of lens swelling.

In accordance with the present invention, the subject ophthalmic solution is a multi-purpose solution effective in disinfecting contact lenses. The subject ophthalmic solution is used for treating contact lenses prior to placement in the eye or is used by administering in the form of drops in the eye, or is used for packaging contact lenses. For this purpose, solutions of the present invention may include one or more antimicrobial agents as a disinfectant or preservative. Suitable antimicrobial agents include for example but are not limited to 1,1'-hexamethylene-bis[5-(p-chlorophenyl)biguanide] (Chlorhexidine), water soluble salts of chlorhexidine, 1,1'-hexamethylene-bis[5-(2-ethylhexyl)biguanide] (Alexidine), water soluble salts of alexidine, poly (hexamethylene biguanide), water soluble salts of poly (hexamethylene biguanide), quaternary ammonium esters and the like. Biguanides are described in U.S. Pat. Nos. 5,990,174; 4,758,595 and 3,428,576 each incorporated herein in its entirety by reference. The preferred biguanide due to its ready commercial availability is poly(aminopropyl biguanide) (PAPB), also commonly referred to as poly (hexamethylene biguanide) (PHMB).

Solutions of the present invention have a pH of about 6.0 to 8.0, and more preferably a pH of about 6.5 to 7.8. To adjust the final pH, one or more suitable buffers may be added to the subject solutions such as but not limited to ethanolamine, diethanolamine, triethanolamine, tromethamine, borate, citrate, phosphate, bicarbonate, and various mixed buffers or buffer systems. Generally, buffers will be used in amounts ranging from about 0.05 to 2.5 percent by weight, and preferably from 0.1 to 1.5 percent by weight.

Typically, ophthalmic solutions of the present invention include one or more, but at least one, tonicity adjusting agent, optionally in the form of a buffering agent, for providing an isotonic or close to isotonic solution such that the osmolality is about 200 to 400 mOsm/kg, but preferably about 250 to 350 mOsm/kg. Examples of suitable tonicity adjusting agents include but are not limited to sodium chloride, potassium chloride, dextrose, mannose, glycerin, propylene glycol, calcium chloride and magnesium chloride. These agents are typically used individually in amounts ranging from about 0.01 to 2.5 weight percent and preferably from about 0.1 to about 1.5 weight percent.

It may also be desirable to optionally include in the subject solutions one or more water soluble viscosity builders such as for example but not limited to hydroxypropylmethyl cellulose, hydroxyethyl cellulose, poly(N-vinylpyrrolidone) and poly(vinyl alcohol). Because of their demulcent effect, viscosity builders have a tendency to further enhance the lens wearer's comfort by means of a film on the lens surface cushioning impact against the eye.

The subject solutions are sterilized by heat or sterile filtration and hermetically sealed. If used as a contact lens packaging solution, the solution is sterilized by heat and hermetically sealed in a blister pack with a contact lens. The subject solutions, if heat sterilized and hermetically sealed, may be used in the absence of an antimicrobial agent.

The solutions of the present invention are described in still greater detail in the examples that follow.

EXAMPLE 1

Use of Polyquaternium 16 to Control Polyether Induced Lens Swelling

SureVue™ lenses (Johnson & Johnson) were soaked in the base test solutions identified below in Table 1 for four hours with a specified amount of polyethers added thereto as identified in Column 1 of Table 2 below. The lenses were then placed under a microscope. While under the microscope, the lenses were submerged in the same solution they were previously soaked in for four hours. Using imaging software connected to the microscope, the length of the diameter of the lenses were measured and recorded as set forth below in Table 2. Before measuring and recording, the microscope was first calibrated with a round disc of known 9.6 mm diameter. SureVue™ lenses are 14.0 mm in diameter in the original packaging solution. The Control 1 solutions containing various amount of polyethers were found to increase the lens diameter in a polyether concentration-dependent manner, which was effectively controlled when Luviquat FC550 and FC370 (Polyquaternium 16) were added into the solutions.

TABLE 1

Base Test Solutions - Polyquaternium 16

| Ingredients (w/w %) | Control 1 | Solution A | Solution B |
| --- | --- | --- | --- |
| Boric Acid | 0.85 | 0.85 | 0.85 |
| Sodium Phosphate Monobasic | 0.15 | 0.15 | 0.15 |
| Sodium Phosphate Dibasic | 0.31 | 0.31 | 0.31 |
| HAP* (30%) | 0.1 | 0.1 | 0.1 |
| Sodium Chloride | 0.26 | 0.26 | 0.26 |
| PHMB** | 1.1 ppm | 1.1 ppm | 1.1 ppm |
| Luviquat FC550 | — | 0.02 | — |
| Luviquat FC370 | — | — | 0.02 |
| pH | 7.0 | 7.0 | 7.0 |
| Osmolality (mOsm/Kg) | 286 | 286 | 286 |

*HAP = Hydroxyalkyl phosphonate
**PHMB = Poly(hexamethylene biguanide)

TABLE 2

Test Results

| | | Lens diameter after 4 hr soaking in the base test solution containing various amount of polyethers (millimeters) | |
| --- | --- | --- | --- |
| Amount of Polyethers Added to the Base Solution | Control 1 | Solution A (Control 1 + Luviquat FC550) | Solution B (Control 1 + Luviquat FC370) |
| 0% Polyethers | 14.23 | 14.02 | 14.06 |
| 1% PT | 14.23 | 13.98 | 14.02 |
| 2% PT | 14.27 | 14.02 | 14.04 |
| 3% PT | 14.27 | 13.98 | 14.08 |
| 5% PT | 14.36 | 14.06 | 14.02 |
| 5% P | 14.32 | 13.98 | 14.04 |

P = Pluronic ™ F127
PT = Mixture of Pluronic F127 and Tetronic 1107 at a 2:1 ratio

EXAMPLE 2

Use of Polyquaternium 10 to Control Polyether Induced Lens Swelling

To further illustrate the effect of cationic polyelectrolytes in controlling polyether induced lens swelling, the base test solutions identified in Table 3 below were tested according to the test procedures described in Example 1 above. The test results are summarized below in Table 4. Polyquaternium-10 compounds, represented here by Polymer JR 400, Polymer LR 400 and Polymer LK, were found to be effective in controlling the lens swelling.

TABLE 3

Base Test Solutions - Polyquaternium 10

| Ingredients (w/w %) | Solution C | Solution D | Solution E |
| --- | --- | --- | --- |
| Boric Acid | 0.85 | 0.85 | 0.85 |
| Sodium Phosphate Monobasic | 0.15 | 0.15 | 0.15 |
| Sodium Phosphate Dibasic | 0.31 | 0.31 | 0.31 |
| HAP* (30%) | 0.1 | 0.1 | 0.1 |
| Sodium Chloride | 0.26 | 0.26 | 0.26 |
| PHMB** | 1.1 ppm | 1.1 ppm | 1.1 ppm |
| Polymer JR 400 | 0.02 | — | — |
| Polymer LR 400 | — | 0.02 | — |
| Polymer LK | — | — | 0.02 |
| pH | 7.0 | 7.0 | 7.0 |
| Osmolality (mOsm/Kg) | 286 | 286 | 286 |

*HAP = Hydroxyalkyl phosphonate
**PHMB = Poly(hexamethylene biguanide)

TABLE 4

Test Results

| | | Lens diameter after 4 hr soaking in the base test solution containing various amount of polyethers (millimeters) | | |
| --- | --- | --- | --- | --- |
| Amount of PPO-PEO Block Polymers Added to the Base Solution | Control 1 | Solution C (Control 1 + JR 400) | Solution D (Control 1 + LR 400) | Solution E (Control 1 + LK) |
| No Polymer (control) | 14.23 | 14.15 | 14.11 | 14.11 |

TABLE 4-continued

Test Results

| Amount of PPO-PEO Block Polymers Added to the Base Solution | Lens diameter after 4 hr soaking in the base test solution containing various amount of polyethers (millimeters) | | | |
|---|---|---|---|---|
| | Control 1 | Solution C (Control 1 + JR 400) | Solution D (Control 1 + LR 400) | Solution E (Control 1 + LK) |
| 1% PT | 14.27 | 14.15 | 14.11 | 14.19 |
| 2% PT | 14.32 | 14.23 | 14.11 | 14.19 |
| 3% PT | 14.27 | 14.23 | 14.23 | 14.19 |
| 5% PT | 14.27 | 14.27 | 14.23 | 14.19 |
| 5% P | 14.40 | 14.27 | 14.32 | 14.27 |

P = Pluronic ™ F127
PT = Mixture of Pluronic F127 and Tetronic 1107 at a 2:1 ratio

EXAMPLE 3

Preferred Formulation with a Borate-Phosphate Buffer

The multi-purpose lens care formulation identified as Solution F in Table 5 below, is illustrative of a preferred embodiment of the present invention using a borate-phosphate buffer.

TABLE 5

Preferred Formulation

| Solution F | Amount (% w/w) |
|---|---|
| Boric Acid | 0.85 |
| Sodium Phosphate Monobasic | 0.15 |
| Sodium Phosphate Dibasic | 0.31 |
| Sodium Chloride | 0.26 |
| Pluronic F127 | 2.0 |
| Tetronic 1107 | 1.0 |
| HAP* (30%) | 0.1 |
| Polymer JR 30M | 0.02 |
| PHMB** | 1.1 ppm |
| pH | 7.0 |
| Osmolality (mOsm/Kg) | 300 |

*HAP = Hydroxyalkyl phosphonate
**PHMB = Poly(hexamethylene biguanide)

EXAMPLE 4

Preferred Formulations with a Triethanolamine Buffer

The following multi-purpose lens care formulations identified as Solutions G through J in Table 6 below, are illustrative of preferred embodiments of the present invention using a triethanolamine buffer.

TABLE 6

Preferred Formulations

| Ingredients (w/w %) | Control 2 | Solution G | Solution H | Solution I | Solution J |
|---|---|---|---|---|---|
| Triethanolamine 99% | 1.356 | 1.356 | 1.356 | 1.356 | 1.356 |
| Pluronic F127 | 1 | 1 | 1 | 1 | 1 |
| Pluronic P123 | 0.2 | 0.2 | 0.2 | 0.2 | 0.2 |
| EDTA* | 0.025 | 0.025 | 0.025 | 0.025 | 0.025 |
| NaCl | 0.159 | 0.159 | 0.159 | 0.159 | 0.159 |
| 1 N HCl | Adjust to pH7.1 | Adjust to pH7.1 | Adjust to pH7.1 | Adjust to pH7.1 | Adjust to pH7.1 |
| PHMB** | 1 ppm | 1 ppm | 1 ppm | 1 ppm | 1 ppm |
| Polymer JR 30M | 0 | 0.02 | 0 | 0 | 0 |
| Polymer JR 400 | 0 | 0 | 0.02 | 0 | 0 |
| Polymer LR 400 | 0 | 0 | 0 | 0.02 | 0 |
| Polymer LK | 0 | 0 | 0 | 0 | 0.02 |
| pH | 7.14 | 7.14 | 7.14 | 7.14 | 7.14 |
| Osmolality (mOsm/Kg) | 220 | 221 | 220 | 219 | 221 |

*EDTA = Ethylenediaminetetraacetic acid, sodium salt
**PHMB = Poly(hexamethylene biguanide)

EXAMPLE 5

Microbiocidal Efficacy Study

To further illustrate the utility of the present invention, a test was conducted to study the microbiocidal efficacy of solutions prepared according to the present invention identified above in Examples 3 and 4. The antimicrobial efficacy of each of the various compositions for the chemical disinfection of contact lenses was evaluated in the presence of 10% organic soil. Microbial challenge inoculums were prepared using *Pseudomonas aeruginosa* (ATCC 9027), *Staphylococcus aureus* (ATCC 6538), *Serratia marcescens* (ATCC 13880), *Candida albicans* (ATCC 10231) and

*Fusarium solani* (ATCC 36031). The test organisms were cultured on appropriate agar and the cultures were harvested using sterile Dulbecco's Phosphate Buffered Saline plus 0.05 percent weight/volume polysorbate 80 (DPBST) or a suitable diluent and transferred to a suitable vessel. Spore suspensions were filtered through sterile glass wool to remove hyphal fragments. *Serratia marcescens*, as appropriate, was filtered through a 1.2 μm filter to clarify the suspension. After harvesting, the suspension was centrifuged at no more than 5000×g for a maximum of 30 minutes at 20 to 25 degrees Celsius. The supernatant was poured off and resuspended in DPBST or other suitable diluent. The suspension was centrifuged a second time, and resuspended in DPBST or other suitable diluent. All challenge bacterial and fungal cell suspensions were adjusted with DPBST or other suitable diluent to $1 \times 10^7$ to $1 \times 10^8$ cfu/mL. The appropriate cell concentration may be estimated by measuring the turbidity of the suspension, for example, using a spectrophotometer at a preselected wavelength, for example 490 nm. One tube was prepared containing a minimum of 10 mL of test solution per challenge organism. Each tube of the solution to be tested was inoculated with a suspension of the test organism sufficient to provide a final count of $1 \times 10^5$ to $1 \times 10^6$ cfu/mL, the volume of the inoculum not exceeding 1 percent of the sample volume. Dispersion of the inoculum was ensured by vortexing the sample for at least 15 seconds. The inoculated product was strored at 10 to 25 degrees Celsius. Aliquots in the amount of 1.0 mL were taken of the inoculated product for determination of viable counts after certain time periods of disinfection. The time points for the bacteria were, for example 1, 2, 3 and 4 hours when the proposed regimen soaking time was four hours. Yeast and mold were tested at an additional timepoint of 16 hours (4 times the regimen time). The suspension was mixed well by vortexing vigorously for at least 5 seconds. The 1.0 mL aliquots removed at the specified time intervals were subjected to a suitable series of decimal dilutions in validated neutralizing media. The suspensions were mixed vigorously and incubated for a suitable period of time to allow for neutralization of the microbial agent. The viable count of organisms was determined in appropriate dilutions by preparation of triplicate plates of trypticase soy agar (TSA) for bacteria and Sabouraud dextrose agar (SDA) for mold and yeast. The bacterial recovery plates were incubated at 30 to 35 degrees Celsius for two to four days. The yeast recovery plates were incubated at 20 to 30 degrees Celsius for two to four days. The mold recovery plates were incubated at 20 to 25 degrees Celsius for three to seven days. The average number of colony forming units was determined on countable plates. Countable plates refer to 30 to 300 cfu/plates for bacteria and yeast, and 8 to 80 cfu/plate for mold except when colonies are observed only for the $10^0$ or $10^{-1}$ dilution plates. The microbial reduction was then calculated at the specified time points. In order to demonstrate the suitability of the medium used for growth of the test organisms and to provide an estimation of the initial inoculum concentration, inoculum controls were made by dispersing an identical aliquot of the inoculum into a suitable diluent, for example DPBST, using the same volume of diluent used to suspend the organism as listed above. Following inoculation in a validated neutralizing broth and incubation for an appropriate period of time, the inoculum control must be between $1.0 \times 10^5$ to $1.0 \times 10^6$ cfu/mL.

The solutions were evaluated based on the performance requirement referred to as the "Stand-Alone Procedure for Disinfecting Products" (hereinafter the "stand-alone test") and is based on the Disinfection Efficacy Testing for Products dated May 1, 1997, prepared by the U.S. Food and Drug Administration, Division of Ophthalmic Devices. This performance requirement does onot contain a rub procedure. This performance requirement is comparable to current ISO standards for disinfection of contact lenses (revised 1995). The stand-alone test challenges a disinfecting product with a standard inoculum of a representative range of microorganisms and establishes the extent of viability loss at predetermined time intervals comparable with those during which the product may be used. The primary criteria for a given disinfection period (corresponding to a potential minimum recommended disinfection period) is that the number of bacteria recovered per mL must be reduced by a mean value of not less than 3.0 logs within the given disinfection period. The number of mold and yeast recovered per ml must be reduced by a mean value of not less than 1.0 log within the minimum recommended disinfection time with no increase at four times the minimum recommended disinfection time. Results of the microbiocidal study are set forth below in Table 7. All forumlations tested passed the primary criteria.

TABLE 7

Results of the Microbiocidal Study
(10% organic soil was used in the test)

Log reduction after 4 hr of exposure to solution

|  | Control 2 | Solution F | Solution G | Solution H | Solution I | Solution J |
|---|---|---|---|---|---|---|
| *S. Aureus* | >4.7 | >4.7 | 4.2 | 4.5 | 4.7 | >4.7 |
| *P. Aeruginosa* | 4.5 | >4.7 | 3.3 | >4.5 | 4.3 | >4.5 |
| *S. Marcescens* | 4.5 | >4.8 | 3.6 | 3.2 | 3.2 | >4.5 |
| *C. Albicans* | 1.5 | 2.5 | 2.4 | 1.2 | 1.6 | 1.6 |
| *F. Solani* | 3.4 | 4.0 | 3.6 | 2.2 | 2.4 | 3.1 |

While there is shown and described herein ophthalmic solutions, hydrogel substrates and methods of making and using the same, it will be manifest to those skilled in the art that various modifications may be made without departing from the spirit and scope of the underlying inventive concept. The present invention is likewise not intended to be limited to particular ophthalmic solutions, substrates or methods described herein except insofar as indicated by the scope of the appended claims.

We claim:

1. A method of reducing swelling in a hydrogel contact lens comprising:
    contacting a hydrogel contact lens with a solution comprising one or more polyethers in an amount ranging from about 2 wt. % to about 5 wt. % and polyquaternium-10 to absorb the solution into the hydrogel contact lens; and
    placing the contact lens into the eye, wherein the solution is released over a period of time from the contact lens and prevents swelling of the contact lens over said period of time.

2. The method of claim 1 wherein said solution contains about 0.001 to 5 percent by weight polyquaternium-10.

3. The method of claim 1 wherein said solution contains about 0.01 to 0.5 percent by weight polyquaternium-10.

4. The method of claim 1 wherein said solution has a pH of about 6.0 to 8.0.

5. The method of claim 1 wherein said solution has a pH of about 6.5 to 7.8.

6. The method of claim 1 wherein said solution includes about 0.05 to 2.5 percent by weight buffer.

7. The method of claim 1 wherein said solution includes about 0.1 to 1.5 percent by weight buffer.

8. The method of claim 1 wherein said solution includes one or more buffers selected from the group consisting of ethanolamine, diethanolamine, triethanolamine, tromethamine, borate, citrate, phosphate and bicarbonate.

9. The method of claim 1 wherein said solution includes one or more tonicity adjusting agents selected from the group consisting of sodium chloride, potassium chloride, dextrose, mannose, gycerin, propylene glycol, calcium chloride and magnesium chloride.

10. The method of claim 1 wherein said solution includes about 0.01 to 2.5 percent by weight tonicity adjusting agent.

11. The method of claim 1 wherein said solution includes about 0.1 to 1.5 percent by weight tonicity adjusting agent.

12. The method of claim 1 wherein said solution includes one or more viscosity builders.

13. The method of claim 1 wherein said solution includes one or more viscosity builders selected from the group consisting of hydroxypropylmethyl cellulose, hydroxyethyl cellulose, poly(N-vinylpyrrolidone) and poly(vinyl alcohol).

14. The method of claim 1 wherein said solution has an osmolality of about 200 to 400 mOsm/kg.

15. The method of claim 1 wherein said solution has an osmolality of about 250 to 350 mOsm/kg.

16. The method of claim 1 wherein said polyethers are based upon poly(ethylene oxide)-poly(propylene oxide)-poly(ethylene oxide) and poly(propylene oxide)-poly(ethylene oxide)-poly(propylene oxide).

* * * * *